United States Patent
González De La Peña et al.

(10) Patent No.: US 8,440,177 B2
(45) Date of Patent: May 14, 2013

(54) METHOD OF TREATING GRAFT VERSUS HOST DISEASE USING ADIPOSE DERIVED MESENCHYMAL STEM CELLS

(75) Inventors: Manuel Angel González De La Peña, Madrid (ES); Dirk Büscher, Madrid (ES); Aitor Beraza Pérez, Madrid (ES); Juan Bueren Roncero, Madrid (ES); Rosa Maria Yanez González, Madrid (ES); Maria Lamana Luzuriaga, Madrid (ES)

(73) Assignees: Centro de Investigaciones Energéticas, Medioambientales y Technológicas, Madrid (ES); TiGenix, SA, Madrid (ES)

( * ) Notice: Subject to any disclaimer, the term of this patent is extended or adjusted under 35 U.S.C. 154(b) by 930 days.

(21) Appl. No.: 12/096,456

(22) PCT Filed: Dec. 7, 2006

(86) PCT No.: PCT/EP2006/069426
§ 371 (c)(1),
(2), (4) Date: Feb. 18, 2009

(87) PCT Pub. No.: WO2007/065927
PCT Pub. Date: Jun. 14, 2007

(65) Prior Publication Data
US 2009/0148419 A1   Jun. 11, 2009

(30) Foreign Application Priority Data
Dec. 7, 2005   (EP) ................... 05380266

(51) Int. Cl.
*A01N 63/00*   (2006.01)
*C12N 5/00*   (2006.01)

(52) U.S. Cl.
USPC ........................ 424/93.1; 435/325

(58) Field of Classification Search .......... 435/325; 424/93.1
See application file for complete search history.

(56) References Cited

FOREIGN PATENT DOCUMENTS
WO   99/47163 A2   9/1999

OTHER PUBLICATIONS

Yanez (47th Annual Meeting of the American society of hematology, Atlanta, GA, Dec. 10-13, 2005, vol. 106, No. 11, Part 1p. 866A.*
Puissant (British J. Haematology, Apr. 2005, vol. 129, No. 1, p. 118-129).*
Gimble (Current topics in Developmenatl Biology, Academic Press, New York, NY, US, 2003, vol. 58, p. 137-160).*
Jorgensen (Gene Therapy, 2003, vol. 10, p. 928-931).*
Sudres (J. Immunol., 2006, vol. 176, p. 7761-7767).*
DeUgarte (Cells Tissues Organs, 2003, vol. 174, p. 101-109).*
Barry (International J. Biochem. & Cell Biology, 2004, vol. 36, p. 568-584).*
Barry, Frank P., Mesenchymal stem cells: clinical applications and biological characterization, The International Journal of Biochemistry & Cell Biology, 2004, pp. 568-582, vol. 36.
Gimble, Jeffrey M., Adipose tissue-derived therapeutics, Expert Opinion on Biological Therapy, 2003, pp. 705-713, vol. 3, No. 5.
Gimble, Jeffrey M., et al., Differentiation Potential of Adipose Derived Adult Stem (ADAS) Cells, Current Topics in Developmental Biology, 2003, pp. 137-160, vol. 58.
Puissant, Benedicte, et al., Immunomodulatory effect of human adipose tissue-derived adult stem cells: comparison with bone marrow mesenchymal stem cells, 2005, pp. 118-129, vol. 129, No. 1.
De Ugarte, Daniel A., et al., Comparison of Multi-Lineage Cells from Human Adipose Tissue and Bone Marrow, 2003, pp. 101-109, vol. 174, No. 3.
Yanez, Rosa M., In Vitro and In Vivo Immunomodulatory Effects of Mesenchylmal Stem Cells from Adipose Tissue, 2005, Abstract.
Zuk, Patricia A., et al., Human Adipose Tissue is a Source of Multipotent Stem Cells, 2002, pp. 4279-4295, vol. 13.

* cited by examiner

*Primary Examiner* — Michael C. Wilson
(74) *Attorney, Agent, or Firm* — Tristan A. Fuierer; Marianne Fuierer; Moore & Van Allen, PLLC

(57) ABSTRACT

The present invention relates to the use of a particular type of adipose tissue derived mesenchymal stem cells (AD-MSCs), which exert immunosuppressive properties, in the manufacture of a pharmaceutical composition for the prevention and treatment of the graft-versus-host disease (GVHD) produced after allogeneic hematopoietic stem cell transplantation.

7 Claims, 9 Drawing Sheets

A

B

A

B

METHOD OF TREATING GRAFT VERSUS HOST DISEASE USING ADIPOSE DERIVED MESENCHYMAL STEM CELLS

CROSS-REFERENCE TO RELATED APPLICATIONS

This application is filed under the provisions of 35 U.S.C. §371 and claims the priority of International Patent Application No. PCT/Ep2006/069426 filed on 7 Dec. 2006 entitled "Use of Adipose Tissue Derived Mesenchymal Stem Cells for the Treatment of Graft Versus Host Disease" in the name of Manuel Angel González de la Peña, et al., which claims priority of European Patent Application No. EP05380266.6 filed on 7 Dec. 2005, both of which are hereby incorporated by reference herein in their entirety.

FIELD OF THE INVENTION

The present invention relates to the prevention and/or treatment of the graft-versus-host disease (GVHD) utilizing a cell population derived from adipose tissue.

BACKGROUND OF THE INVENTION

GVHD is a syndrome observed after allogeneic hematopoietic stem cell transplantation (HSCT) and mediated by immunocompetent donor T lymphocytes reactive against the tissues of the recipient.

Increasingly, HSCT is used to treat hematologic malignancies, and other diseases such as aplastic anemia, solid tumors and autoimmune disorders. HSCT remains a powerful treatment option that offers a true chance for a cure of many diseases. Introducing hematopoietic cells into an immunoablated host with successful marrow engraftment, with maintenance of an antitumor effect (if applicable), and without GVHD is the goal of many investigators. GVHD remains, however, as the primary cause of morbidity and mortality in hematopoietic cell recipients.

GVHD can be acute or chronic. Acute GVHD develops in 35-50% of patients given HLA-identical marrow grafts within the first 100 days of transplantation. The main target organs are skin, liver, and intestinal tract. Approximately one half of the patients with moderately severe to severe disease die, usually from associated infections.

Prevention of acute GVHD by immunosuppressive treatment after grafting, or removal of donor lymphocytes from the marrow inoculum has, as yet, not been uniformly successful. Treatment of established GVHD involves the use of immunosuppressors such as glucocorticosteroids, antithymocyte globulin, cyclosporine, and monoclonal antibodies. However, these approaches increase the risk of engraftment failures, delayed immune reconstitution, viral infections and relapses of the original malignant disease.

Chronic GVHD usually develops 100-500 days after transplantation and affects about 45% of all long-term survivors and it is characterized by symptoms similar to those observed for autoimmune disease. The main target organs are the same as those of acute GVHD and, in addition, lacrimal and salivary glands, mucous and serous membranes are also affected. The clinical picture resembles that of a number of collagen-vascular diseases. The incidence of chronic GVHD is higher in patients with previous acute GVHD and it increases with the patient age. Actual treatments involve the use of immunosuppressors and cytotoxic drugs. These approaches increase the risk of engraftment failures, delayed immune reconstitution, viral infections and relapses of the original malignant disease.

On the other hand, in vitro and in vivo immunosuppressive properties of bone marrow derived mesenchymal stem cells (BM-MSCs) have been reported. Said BM-MSCs are negative for the hematopoietic stem cell and endothelial CD34 marker antigen. The immunosuppressive properties of BM-MSCs strengthen the clinical relevance of said cells in allogenic transplantation by reducing the incidence and severity of GVHD [Jorgensen C. et al., (2003) Gene Therapy, 10, 928-931]. However, the use of BM-MSCs has a number of drawbacks such as they are obtained from a donor through an aggressive intervention that requires the general anaesthesia of the donor, sufficient BM-MSCs may not be obtained from some donors (particularly from older donors or those with malignant diseases), BM-MSCs are present in very low numbers in bone marrow, bone marrow aspirates are mostly dedicated to transplantation of haematopoietic stem cells, and BM-MSCs display a low in vitro proliferative potential, and, consequently, the generation of a therapeutically effective dose of said cells is relatively slow. Consequently, there is a need for an alternative source of mesenchymal cells for the treatment of GVHD.

The inventors have now found that adipose tissue derived mesenchymal stem cells can be used for the prevention and/or treatment of GVHD. Adipose tissue derived mesenchymal stem cells (AD-MSCs) are mesenchymal stem cells (MSCs) that can be obtained from adipose tissue, e.g., from aspirates of adipose tissue. A method for the isolation and ex vivo expansion of AD-MSCs is disclosed in PCT/EP2005/010811. This patent application also discloses the phenotypic characterization of the AD-MSCs cell population by cell surface markers profile determination. As it is the case for BM-MSCs, the disclosed AD-MSCs are characterized to be predominantly negative for the hematopoietic stem cell and the endothelial CD34 marker antigen. The use of said AD-MSCs for repairing and regenerating tissues is disclosed therein. Recently, some researchers claimed to have generated immunosuppressive mesenchymal stem cells termed ADAS cells (adipose tissue derived adult stem cells) which share immunomodulatory properties with BM-MSCs. The researchers suggest that, similar to BM-MSCs, the infusion of said ADAS cells could decrease GVDH in allogeneic bone marrow transplantation [Puissant B. et al., (2005) British Journal of Haematology, 129, 118-129]. Said ADAS cells are, however, different from BM-MSCs, and also from AD-MSCs. In fact, the authors point out that in contrast to BM-MSCs, ADAS cells used in the functional test were positive for the hematopoietic stem cell and endothelial CD34 marker antigen, although the CD34$^+$ staining on ADAS cells decreased according to passages.

SUMMARY OF THE INVENTION

The graft versus host disease (GVHD) is the major peritransplant complication associated to the transplantation of allogeneic progenitor cells in patients. The present invention relates to a novel method for the prevention and/or the treatment of GVHD using a population of cells derived from adipose tissue, namely, the adipose tissue derived mesenchymal stem cells (AD-MSCs). Said AD-MSCs are phenotypically characterized in that they are (i) negative for at least one, two, three, four, five, six, seven, eight, nine, ten or preferably all of the following markers CD3, CD11b, CD 14, CD19, CD31, CD34, CD45, CD62L, CD95L, CD117, and HLA-DR, and (ii) positive for at least one, two, three, four, five, six, seven, eight or preferably all of the following markers CD13, CD29, CD44, CD49e, CD73, CD90, CD105, CD166, and HLA-ABC.

The AD-MSCs cells of the present invention are predominantly negative for the hematopoietic stem cell and endothelial CD34 marker antigen, as is the case for BM-MSCs. The AD-MSCs cells of the invention may preferably be at least 50%, 60%, 70%, 80%, 90%, 95%, 99% or more CD34$^-$.

The invention is based on the findings that, in vitro, said AD-MSCs are not immunogenic and have immunosuppressive effects, similar to those observed for BM-MSCs, and that, in vivo, in an allogeneic HSCT mouse model, said AD-MSCs can ameliorate the severity of the GVHD and reduce the mortality associated to GVHD. Therefore, the observations of the inventors indicate that AD-MSCs can constitute a new cellular reactive for the prevention and/or treatment of the GVHD associated to the transplantation of hematopoietic grafts.

Inventors have surprisingly found that said AD-MSCs share immunosuppressive properties with BM-MSCs but overcome the drawbacks associated with said cells. In fact, the therapeutic use of AD-MSCs requires large quantities of cells for, e.g., infusion. A large quantity of AD-MSCs can be obtained, for example, by simple lipoaspiration (lipectomy), from an aspirate of adipose tissue, which is currently performed with local anaesthesia on healthy people; further, large quantities of lipoaspirate samples from aesthetic interventions—which nowadays are thrown away—could be collected for the growth of AD-MSCs, and preserved frozen for the creation of AD-MSCs banks. Since these cells are not immunogenic, these cells could also be used for the treatment of a number of diseases. Moreover, cultured AD-MSCs seem to display an increased in vitro proliferative potential compared with BM-MSCs and could generate a therapeutically effective dose of said cells more rapidly than the same number of BM-MSCs. Therefore, the therapeutic use of AD-MSCs has a number of advantages compared to BM-MSCs.

Thus, in an aspect, the invention relates to the use of said AD-MSCs cell population in the manufacture of a pharmaceutical composition for the prevention and treatment of GVHD.

In other aspect, the invention relates to a method of preventing and/or treating GVHD in a subject suffering from said disease, which comprises administering to said subject in need of such treatment of a prophylactically or therapeutically effective amount of said AD-MSCs cell population.

The invention also relates to the use of such methods in combination therapy, in other words, a cell population of the invention is co-administered with one or more agents, either simultaneously with the second or further agent, or separately, e.g., sequentially.

DETAILED DESCRIPTION OF THE INVENTION

Figure 1:
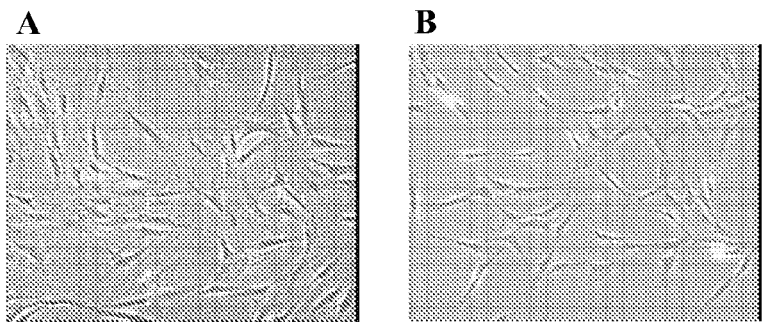
FIG. 1 shows two microscopically pictures in which morphology of (A) human adipose tissue derived mesenchymal stem cells (hAD-MCs) and (B) human bone marrow mesenchymal stem cells (hBM-MCs), are illustrated.

The present invention refers, in general, to a new treatment for graft-versus-host disease (GVHD). The inventors have found that a certain cell population, which is present in adipose tissue, namely adipose tissue derived mesenchymal stem cells (AD-MSCs), is effective for the treatment of said disease. Therefore, said cell population can be used in the manufacture of a pharmaceutical composition for the prevention and/or treatment of GVHD.

DEFINITIONS

In order to facilitate the understanding of the present description, the meaning of some terms and expressions in the context of the invention will be explained below. Further definitions will be included along the description when necessary.

It is to be noted that in the normal situation for inducing tolerance of an allogeneic solid organ transplant, the clinical focus is on preventing the immune system of the recipient (host) from attacking the donor's organ (graft). The present invention relates to the reversed situation, distinct from conventional host-mediated rejection of transplanted organs and tissues, in which immune cells derived from the donor's hematopoietic tissue (graft) are attacking the recipient's (host) tissue or organs.

Thus the term "graft versus host disease" or "GVHD" refers to a syndrome observed after allogeneic hematopoietic stem cell transplantation (HSCT) and presumably mediated by immunocompetent donor immune cells, for example, T lymphocytes reactive against the tissues of the recipient. GVHD can be acute or chronic.

The term "subject" refers to an animal, preferably a mammal including a non-primate (e.g., a cow, pig, horse, cat, dog, rat, or mouse) and a primate (e.g., a monkey, or a human). In a preferred embodiment, the subject is a human.

The term "isolated" applied to a cell population refers to a cell population, isolated from the human or animal body, which is substantially free of one or more cell populations that are associated with said cell population in vivo or in vitro.

The term "adipose tissue derived mesenchymal cells" or "AD-MSCs", as used herein, refers to cells that originate from adipose tissue and are phenotypically characterized in that they are (i) negative for at least one, two, three, four, five, six, seven, eight, nine, ten or preferably all of the following markers CD3, CD11b, CD 14, CD19, CD31, CD34, CD45, CD62L, CD95L, CD117, and HLA-DR cell surface markers, and (ii) positive for at least one, two, three, four, five, six, seven, eight or preferably all of the following markers CD13, CD29, CD44, CD49e, CD73, CD90, CD105, CD166, and HLA-ABC cell surface markers. By "adipose tissue" is meant any fat tissue. The adipose tissue may be brown or white adipose tissue, derived from subcutaneous, omental/visceral, mammary, gonadal, or other adipose tissue site, e.g., the adipose tissue is subcutaneous white adipose tissue.

As used herein, the terms "treat", "treatment" and "treating" refer to the amelioration, cure or remedy of GVHD, which results from the administration of the pharmaceutical composition provided by the present invention comprising said population of AD-MSCs to a subject in need of said treatment.

The term "combination therapy" refers to the use of the cell populations of the present invention with other active agents or treatment modalities, in the manner of the present invention for the amelioration of one or more symptoms associated with a disorder including, but not limited to, an inflammatory disorder, an autoimmune disease or an immunologically mediated disease including rejection of transplanted organs and tissues. These other agents or treatments may include known drugs and therapies for the treatment of such disorders. The cell populations of the invention may also be combined with corticosteroids, non-steroidal anti-inflammatory compounds, or other agents useful in treating inflammation. The combined use of the agents of the present invention with these other therapies or treatment modalities may be concurrent, or given sequentially, that is, the two treatments may be divided up such that a cell population or a pharmaceutical composition comprising same of the present invention may be given prior to or after the other therapy or treatment modality. The attending physician may decide on the appropriate sequence of administering the cell population, or a pharmaceutical composition comprising same, in combination with other agents, therapy or treatment modality.

Use of AD-MSCs for Preventing and/or Treating GVHD

The present invention is based on the finding that a cell population of AD-MSCs can be used for preventing and/or treating GVHD.

Thus, in an aspect, the invention relates to the use of an AD-MSCs population, hereinafter referred to as AD-MSCs population of the invention, characterised in that the cells of said cell population are (i) negative for at least one, two, three, four, five, six, seven, eight, nine, ten or preferably all of the following markers CD3, CD11b, CD14, CD19, CD31, CD34, CD45, CD62L, CD95L, CD117, and HLA-DR cell surface markers and (ii) positive for at least one, two, three, four, five, six, seven, eight or preferably all of the following markers CD13, CD29, CD44, CD49e, CD73, CD90, CD 105, CD 166, and HLA-ABC cell surface markers for the prevention and/or treatment of GVHD. The cells of the AD-MSCs population further present capacity to be differentiated in one or more cell lineages.

Cells

The cells of the AD-MSCs population of the invention are negative for at least one, two, three, four, five, six, seven, eight, nine, ten or preferably all of the following markers CD3, CD11b, CD14, CD19, CD31, CD34, CD45, CD62L, CD95L, CD117, and HLA-DR cell surface markers. As used herein, "negative" with respect to cell surface markers means that, in a cell population comprising the cells of the invention, less than 10%, preferably 9%, 8%, 7%, 6%, 5%, 4%, 3%, 2%, 1% or none of the cells show a signal for a specific cell surface marker in flow cytometry above the background signal, using conventional methods and apparatus (for example, a Beckman Coulter Epics XL FACS system used with commercially available antibodies and standard protocols known in the art).

In a particular embodiment, the cells of the invention are characterised in that they express at least one, two, three, four, five, six, seven, eight or preferably all of the following markers CD13, CD29, CD44, CD49e, CD73, CD90, CD105, CD166, and HLA-ABC; i.e., the cells of the AD-MSCs population of the invention are positive for at least one, two, three, four, five, six, seven, eight or preferably all of said cell surface markers (CD13, CD29, CD44, CD49e, CD73, CD90, CD105, CD166, and HLA-ABC). Preferably, the cells of the AD-MSCs population of the invention are characterised in that they have significant expression levels of at least one, two, three, four, five, six, seven, eight and preferably all of said cell surface markers (CD13, CD29, CD44, CD49e, CD73, CD90, CD105, CD166, and HLA-ABC). As used herein, the expression "significant expression" means that, in a cell population comprising said AD-MSCs, more than 10%, preferably 20%, 30%, 40%, 50%, 60%, 70%, 80%, 90% or all of the cells show a signal for a specific cell surface marker in flow cytometry above the background signal using conventional methods and apparatus (for example, a Beckman Coulter Epics XL FACS system used with commercially available antibodies and standard protocols known in the art). The background signal is defined as the signal intensity given by a non-specific antibody of the same isotype as the specific antibody used to detect each surface marker in conventional FACS analysis. Thus for a marker to be considered positive the specific signal observed is stronger than 10%, preferably 20%, 30%, 40%, 50%, 60%, 70%, 80%, 90%, 500%, 1000%, 5000%, 10000% or above, than the background signal intensity using conventional methods and apparatus (for example, a Beckman Coulter Epics XL FACS system used with commercially available antibodies and standard protocols known in the art).

In particular, it should be noted that the AD-MSCs cells of the present invention are predominantly negative for the hematopoietic stem cell and endothelial CD34 marker antigen. The AD-MSCs cells of the invention may preferably be at least 50%, 60%, 70%, 80%, 90%, 95%, 99% or more CD34$^-$.

Commercially available and known monoclonal antibodies against said cell-surface markers can be used to identify the cells of the AD-MSCs population of the invention.

In a particular embodiment, the cells of the AD-MSCs population of the invention are the cells disclosed by PCT/EP2005/010811.

The cells of the AD-MSCs population of the invention derive from adipose tissue and can be obtained, by conventional techniques known for the skilled person in the art, from any suitable source of adipose tissue from any suitable animal, including humans. In general, said cells are obtained from non-pathological post-natal mammalian adipose tissues. In a preferred embodiment, the cells of the AD-MSCs population of the invention are obtained from a source of adipose tissue, such as the stromal fraction of adipose tissue.

The AD-MSCs can be obtained from any suitable source of adipose tissue from any suitable animal, including humans, having adipose tissue. Preferably, the cells of the AD-MSCs population of the invention are from a mammal, e.g., a rodent, primate, etc., preferably, from a human. A convenient source of adipose tissue is from liposuction surgery. In fact, a large quantity of AD-MSCs can be obtained by simple aspiration from adipose tissue, such as, for example, lipoaspirate samples from aesthetic interventions. Example 1 describes in a detailed manner the isolation of the cells of the AD-MSCs population of the invention from human adipose tissue.

In a particular embodiment, the cells of the AD-MSCs population of the invention are obtained according to the method disclosed by PCT/EP2005/010811.

Cell-surface markers can be identified by any suitable conventional technique, usually based on a positive/negative selection; for example, monoclonal antibodies against cell-surface markers, whose presence/absence in the cells has to be confirmed, can be used; although other techniques can also be used. Thus, in a particular embodiment, monoclonal antibodies against one, two, three, four, five, six, seven, eight, nine, ten or preferably all of CD3, CD11b, CD14, CD19, CD31, CD34, CD45, CD62L, CD95L, CD117, and HLA-DR are used in order to confirm the absence of said markers in the selected cells; and monoclonal antibodies against one, two, three, four, five, six, seven, eight or preferably all of CD13, CD29, CD44, CD49e, CD73, CD90, CD105, CD166, and HLA-ABC are used in order to confirm the presence thereof or detectable expression levels of, at least one of and preferably all of, said markers. Said monoclonal antibodies are known, commercially available or can be obtained by a skilled person in the art by conventional methods.

The cells of the AD-MSCs population of the invention further present the capacity to proliferate and be differentiated into at least two, more preferably three, four, five, six, seven or more cell lineages. Illustrative, non-limiting examples of cell lineages in which said cells can be differentiated include, among others, bone, adipocytes, chondrocytes, tenocytes, myocytes, cardiomyocytes, hematopoietic-supporting stromal cells, endothelial cells, hepatocytes, astrocytes, or neuronal phenotype cells.

The cells of the AD-MSCs population of the invention can proliferate and differentiate into cells of other lineages by conventional methods. Methods for identifying and subsequently isolating differentiated cells from their undifferentiated counterparts can be also carried out by methods well known in the art. The capacity of the cells of the AD-MSCs population of the invention to differentiate into one or more cell lineages can be assayed by conventional methods known by the skilled person in the art.

The cells of the AD-MSCs population of the invention are also capable of being expanded ex vivo. That is, after isolation, said cells can be maintained and allowed to proliferate ex vivo in culture medium. Such medium is composed of, for example, Dulbecco's Modified Eagle's Medium (DMEM), with antibiotics (for example, 100 units/ml Penicillin and 100 μg/ml Streptomycin) or without antibiotics, and glutamine, and supplemented with foetal bovine serum (FBS). It is within the skill of one in the art to modify or modulate concentrations of media and/or media supplements as necessary for the cells used. Sera often contain cellular and non-cellular factors and components that are necessary for viability and expansion. Examples of sera include FBS, bovine serum (BS), calf serum (CS), fetal calf serum (FCS), newborn calf serum (NCS), goat serum (GS), horse serum (HS), porcine serum, sheep serum, rabbit serum, rat serum (RS), etc. Also contemplated is, if the cells of the AD-MSCs population of the invention are of human origin, supplementation of cell culture medium with a human serum, preferably of autologous origin. It is understood that sera can be heat-inactivated at 55-65° C. if deemed necessary to inactivate components of the complement cascade. Modulation of serum concentrations, withdrawal of serum from the culture medium can also be used to promote survival of one or more desired cell types. In another embodiment, the cells of the AD-MSCs population of the invention can be expanded in a culture medium of definite composition, in which the serum is replaced by a combination of serum albumin, serum transferrin, selenium, and recombinant proteins including but not limited to: insulin, platelet-derived growth factor (PDGF), and basic fibroblast growth factor (bFGF), as known in the art.

Many cell culture media already contain amino acids; however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, and the like. Antimicrobial agents are also typically used in cell culture to mitigate bacterial, mycoplasmal, and fungal contamination. Typically, antibiotics or anti-mycotic compounds used are mixtures of penicillin/streptomycin, but can also include, but are not limited to amphotericin, ampicillin, gentamicin, bleomycin, hygromacin, kanamycin, mitomycin, etc. Hormones can also be advantageously used in cell culture and include, but are not limited to, D-aldosterone, diethylstilbestrol (DES), dexamethasone, b-estradiol, hydrocortisone, insulin, prolactin, progesterone, somatostatin/human growth hormone (HGH), etc.

The maintenance conditions of the cells of the AD-MSCs population of the invention can also contain cellular factors that allow cells to remain in an undifferentiated form. It is apparent to those skilled in the art that prior to differentiation supplements that inhibit cell differentiation must be removed from the culture medium. It is also apparent that not all cells will require these factors. In fact, these factors may elicit unwanted effects, depending on the cell type.

If desired, the cells of the AD-MSCs population of the invention can be clonally expanded using a suitable method for cloning cell populations. For example, a proliferated population of cells can be physically picked and seeded into a separate plate (or the well of a multi-well plate). Alternatively, the cells can be subcloned onto a multi-well plate at a statistical ratio for facilitating placing a single cell into each well (e.g., from about 0.1 to about 1 cell/well or even about 0.25 to about 0.5 cells/well, such as 0.5 cells/well). Of course, the cells can be cloned by plating them at low density (e.g., in a Petri dish or other suitable substrate) and isolating them from other cells using devices such as a cloning rings. The production of a clonal population can be expanded in any suitable culture medium. In any event, the isolated cells can be cultured to a suitable point when their developmental phenotype can be assessed.

Further investigations have shown that ex vivo expansion of the cells of the AD-MSCs population of the invention without inducing differentiation can be accomplished for extended time periods for example by using specially screened lots of suitable serum (such as fetal bovine serum or human serum). Methods for measuring viability and yield are known in the art (e.g., trypan blue exclusion).

Any of the steps and procedures for isolating the cells of the AD-MSCs population of the invention can be performed manually, if desired. Alternatively, the process of isolating such cells can be facilitated and/or automated through one or more suitable device, many of which are known in the art.

Pharmaceutical Composition

For the administration in the prevention and/or treatment of GVHD, the cells of the AD-MSCs population of the invention will be formulated in a suitable pharmaceutical composition, hereinafter referred to as the "pharmaceutical composition of the invention", comprising cells of the AD-MSCs population of the invention, in a therapeutically or prophylactically effective amount, together with a suitable pharmaceutically acceptable vehicle.

The particulars of the cells of the AD-MSCs population of the invention have been previously disclosed.

As used herein the term "prophylactically or therapeutically effective amount" refers to the amount of cells of the AD-MSCs population of the invention contained in the pharmaceutical composition which is capable of producing the desired therapeutic effect and, in general, it will be determined, among other factors, by the own cells characteristics and the desired therapeutic effect to be aimed. In general, the therapeutically effective amount of AD-MSCs cells to be administrated will depend, among other factors, on the subject own characteristics, the severity of the disease, the way of administration, etc. For this reason, the mentioned doses in this invention must be only considered as a guide for the skilled person in the art, who must adjust said doses depending on the above described factors. As an illustrative, non limiting, example the pharmaceutical composition of the invention can be administered as an unique dose, containing approximately between $1 \times 10^5$ and $10 \times 10^6$ cells of the AD-MSCs cell population of the invention/kg of the body weight of the recipient, and more preferably between $5 \times 10^5$ and $5 \times 10^6$ cells of the AD-MSCs cell population of the invention/kg of the body weight of the recipient, in an even more preferably embodiment said pharmaceutical composition will contain approximately between $1 \times 10^6$ and $2 \times 10^6$ cells of the AD-MSCs cell population of the invention/kg of the body weight of the recipient, depending on the previously described factors. The dose of cells of the cell population of the invention can be repeated, depending on the patient's condition and evolution, at time intervals of days, weeks or months that have to be established by the specialist in each case.

The cells of the AD-MSCs population of the invention are cells from autologous or allogeneic origin. In a preferred embodiment, the cells are extracted from the adipose tissue of the person into whom they are to be administered, thereby reducing potential complications associated with antigenic and/or immunogenic responses to said cells.

If desired, the cells of the AD-MSCs population of the invention can be purified, as previously mentioned, by use of antibody-mediated positive and/or negative cell selection in order to enrich the cell population to increase efficacy, reduce morbidity, or to facilitate ease of the procedure.

According to the invention, the cells of the AD-MSCs population of the invention can be administered to the patient without further processing or following additional procedures to further purify, modify, stimulate, or otherwise change the cells. For example, the cells obtained from a subject may be administered to a subject in need thereof (patient) without culturing the cells before administering them to the patient. In one embodiment, the collection of adipose tissue will be performed at a patient's bedside. Hemodynamic monitoring may be used to monitor the patient's clinical status. In accordance with the invention herein disclosed, the pharmaceutical composition comprising said AD-MSCs can be delivered to the patient soon after harvesting the adipose tissue from the patient. For example, the pharmaceutical composition of the invention may be administered immediately after the processing of the adipose tissue to obtain a composition of AD-MSCs cells. In one embodiment, the timing of delivery will depend upon patient availability and the processing time required for processing the adipose tissue.

The term "pharmaceutically acceptable vehicle" refers to approved by a regulatory agency of the Federal or a state government or listed in the U.S. Pharmacopeia, or European Pharmacopeia, or other generally recognized pharmacopeia for use in animals, and more particularly in humans. The term "vehicle" refers to a diluent, adjuvant, excipient, or carrier with which the cells of the AD-MSCs population of the invention is administered; obviously, the vehicle must be compatible with the cells. The pharmaceutical composition of the invention, if desired, can also contain, when necessary, additives to enhance, control, or otherwise direct the intended therapeutic effect of the cells comprising said pharmaceutical composition, and/or auxiliary substances or pharmaceutically acceptable substances, such as minor amounts of pH buffering agents, tensioactives, co-solvents, preservatives, etc. Also, for stabilizing the cell suspension, it is possible to add metal chelating agents. The stability of the cells in the liquid medium of the pharmaceutical composition of the invention can be improved by means of adding additional substances, such as, for example, aminoacids such as aspartic acid, glutamic acid, etc. Said pharmaceutically acceptable substances that can be used in the pharmaceutical composition of the invention are known, in general, by the skilled person in the art and are normally used in the manufacture of cellular compositions. Examples of suitable pharmaceutical vehicles are described in "Remington's Pharmaceutical Sciences" by E. W. Martin. Additional information about said vehicles can be found in any handbook of Pharmaceutical Technology (i.e., galenic pharmacy). Illustrative, non limiting, examples of said vehicles for the administration of the cells contained in the pharmaceutical composition of the invention include, for example, a sterile saline solution (0.9% NaCl), PBS, etc.

The pharmaceutical composition of the invention will contain a prophylactically or therapeutically effective amount of the cells of the AD-MSCs population of the invention, preferably in a substantially purified form, together with the suitable vehicle in the appropriate amount in order to provide the form for proper administration to the subject.

The pharmaceutical composition of the invention will be formulated according to the chosen form of administration. The formulation should suit the mode of administration. In a particular embodiment, the pharmaceutical composition is prepared in a liquid dosage form, e.g., as a suspension, to be injected or perfunded into the subject in need of treatment. Illustrative, non limiting examples, include formulating the pharmaceutical composition of the invention in a sterile suspension with a pharmaceutically acceptable vehicle, such as saline solution, phosphate buffered saline solution (PBS), or any other suitable pharmaceutically acceptable carrier, for parenteral administration to a subject, e.g., a human being, preferably via intravenous, intraperitoneal, subcutaneous, etc., although further administration routes may be also possible.

The administration of the pharmaceutical composition of the invention to the subject in need thereof can be carried out by conventional means. In a particular embodiment, said pharmaceutical composition can be administered to the subject in need by intravenous administration using devices such as syringes, catheters, trocars, cannulae, etc. In any case, the pharmaceutical composition of the invention will be administrated using the appropriate equipments, apparatus, and devices which are known by the skilled person in art.

In a particular embodiment, the administration of the pharmaceutical composition of the invention will be via intravenous and will include an intravenous delivery through standard devices, e.g., a standard peripheral intravenous catheter, a central venous catheter, or a pulmonary artery catheter, etc. The flow of cells may be controlled by serial inflation/deflation of distal and proximal balloons located within the patient's vasculature, thereby creating temporary no-flow zones which promote cellular therapeutic action.

In another embodiment, direct administration of the pharmaceutical composition of the invention to the site of intended benefit may be advantageous. As it has been described above, the main target organs for acute GVHD are skin, liver, and intestinal tract. Also, the main target organs for chronic GVHD are the same as those of acute GVHD and, in addition, lacrimal and salivary glands, although mucous and serous membranes are also affected. In this way, direct administration of the pharmaceutical composition of the invention to the desired organ or tissue may be achieved by direct administration, (e.g., by injection, erc.) into the external surface of the affected organ or tissue through insertion of a suitable device, e.g., a suitable cannula, by arterial or venous infusion (including retrograde flow mechanisms) or by other means disclosed herein or known in the art.

As mentioned above, cells of the AD-MSCs population of the invention may be applied by several routes including systemic administration by venous or arterial infusion (including retrograde flow infusion) or by direct injection into the affected organ or tissue. Systemic administration, particularly by peripheral venous access, has the advantage of being minimally invasive relying on the natural perfusion of the heart and the ability of adipose tissue-derived cells to target the site of damage. The pharmaceutical composition containing the cells may be injected in a single bolus, through a slow infusion, or through a staggered series of applications separated by several hours or, provided cells are appropriately stored, several days or weeks. Cells may also be applied by use of catheterization such that the first pass of cells through the heart is enhanced by using balloons to manage myocardial blood flow. As with peripheral venous access, cells may be injected through the catheters in a single bolus or in multiple smaller aliquots.

The pharmaceutical composition containing said cells may be stored until use by means of conventional methods known by the skilled person in the art. Said pharmaceutical composition may also be stored together with additional drugs, useful in the prevention and/or treatment of GVHD, in an active form comprising a combination therapy. For short term storage (less than 6 hours) the pharmaceutical composition containing said cells may be stored at or below room temperature in a sealed container with or without supplementation with a nutrient solution. Medium term storage (less than 48 hours) is preferably performed at 2-8° C., the pharmaceutical composition comprising an iso-osmotic, buffered solution in a container composed of or coated with a material that prevents cell adhesion. Longer term storage is preferably performed by appropriate cryopreservation and storage under conditions that promote retention of cellular function.

In a particular embodiment, the cell populations and pharmaceutical compositions of the invention can be used in a combination therapy. In a particular embodiment, said pharmaceutical composition is administrated in combination with an additional pharmaceutical composition for the treatment of GVHD. Thus, AD-MSCs can be used as a single treatment or combined with other conventional immunosuppressive treatments, such as cyclosporine, methotrexate, corticoids, infliximab, daclizumab, etc., both for the prevention and for the treatment of chronic or acute GVHD [LeBlanc, Lancet, $1^{st}$ May 2004]. Optionally, anti-inflammatory drugs including, but not limited to, non-steroidal anti-inflammatory drugs (NSAIDs) (e.g., ibuprofen, celecoxib, diclofenac, etodolac, fenoprofen, indomethacin, ketoralac, oxaprozin, nabumentone, sulindac, tolmentin, rofecoxib, naproxen, ketoprofen, nabumetone, etc.), steroidal anti-inflammatory drugs (e.g., glucocorticoids, dexamethasone, cortisone, hydrocortisone, prednisone, prednisolone, triamcinolone, azulfidine, eicosanoids, etc.), beta-agonists, anticholingeric agents, and methyl xanthines can be used.

In a specific embodiment, the combination therapy is administered to a subject with GVHD that is refractory to one or more immunosuppressive treatments.

The pharmaceutical composition of the invention can be used in a combination therapy as described above useful in the prevention and/or treatment of GVHD. Said additional drugs can be part of the same pharmaceutical composition or, alternatively, they can be provided in the form of a separate composition for their simultaneous or successive (sequential in time) administration with respect to the administration of the pharmaceutical composition of the invention. In a particular embodiment, said additional pharmaceutical composition is administered simultaneously or sequentially to the pharmaceutical composition comprising the AD-MSCs population, spaced out in time, in any order, i.e. first the pharmaceutical composition of the invention, then the other additional drugs or other pharmaceutical composition for the treatment of GVHD can be administered, or first the other additional drugs or other pharmaceutical composition for the treatment of GVHD and then the pharmaceutical composition of the invention can be administered. Alternatively, any two of said components can be mixed in the same composition and be administered together. In another alternative embodiment said pharmaceutical composition of the invention and other additional drugs or other pharmaceutical composition for the treatment of GVHD are simultaneously administered.

For its administration to a subject, the previously defined product will be formulated in a pharmaceutical administration form, preferably a pharmaceutical administration form suitable for its intravenous administration, to which end the pharmaceutically acceptable carriers and excipients suitable for the preparation of the desired pharmaceutical administration form will be incorporated. Information about said carriers and excipients, as well as about said administration forms suitable for the administration of said product of the invention, can be found in any handbook of Pharmaceutical Technology, e.g., "Tratado de Farmacia Galénica", C. Fauli i Trillo, 10 Edición, 1993, Luzán 5, S.A. de Ediciones. Patients are typically monitored prior to and during the deliver of the pharmaceutical composition of the invention. After delivery of the pharmaceutical composition, patients may require an approximate 24 hour period of monitoring for adverse events. Follow-up studies to assess functional improvements are recommended.

In another aspect, the present invention refers to a method for preventing or treating the graft-versus-host disease (GVHD) in a subject suffering from said disease, said method comprising the administration to the subject in need of such treatment a prophylactically or therapeutically effective amount of a pharmaceutical composition comprising an adipose tissue derived cell population characterised in that (i) the cells of said cell population are negative for at least one, two, three, four, five, six, seven, eight, nine, ten or preferably all of the following markers CD3, CD11b, CD14, CD19, CD31, CD34, CD45, CD62L, CD95L, CD117, and HLA-DR cell surface markers and (ii) are positive for at least one, two, three, four, five, six, seven, eight or preferably all of CD13, CD29, CD44, CD49e, CD73, CD90, CD105, CD166, and HLA-ABC cell surface markers. The cells of the AD-MSCs population further present capacity to be differentiated in one, two more preferably three, four, five, six, seven or more cell lineages.

As used herein, GVHD includes acute GVHD and chronic GVHD. As described above, the administration of the pharmaceutical composition of the invention to the subject in need thereof can be carried out by conventional means. In a particular embodiment, said pharmaceutical composition can be administered to the subject in need of by means of an intravenous administration.

EXAMPLES

The invention will now be described in more detail, by way of examples which in no way are meant to limit the scope of the invention, but, rather, these examples will serve to illustrate the invention with reference to the accompanying figures.

Example 1

Isolation, Expansion and Characterization of Human Mesenchymal Stem Cells

Adipose Tissue-Derived Mesenchymal Stem Cells (hAD-MSCs) and Bone Marrow-Derived Mesenchymal Stem Cells (hBM-MSCs)

1.1 Isolation and Ex Vivo Expansion of Human Adipose Tissue-Derived Mesenchymal Stem Cells (hAD-MSCs)

Isolation of Human Adipose Tissue-Derived Mesenchymal Stem Cells (hAD-MSCs)

Human adipose tissue was obtained by liposuction, under local anaesthesia and general sedation. A hollow blunt-tipped cannula was introduced into the subcutaneous space through a small incision (less than 0.5 cm in diameter). With gentle suction, the cannula was moved through the adipose tissue abdominal-wall compartment for mechanical disruption of the fatty tissue. A saline solution and the vasoconstrictor epinephrine were injected into the adipose tissue compartment to minimize blood loss. In this way, 80-100 ml of raw lipoaspirate was obtained from the human being so treated.

The raw lipoaspirate was washed extensively with sterile phosphate-buffered saline (PBS; Gibco BRL, Paisley, Scotland, UK) to remove blood cells, saline and local anaesthetic. The extracellular matrix was digested with a solution of type II collagenase (0.075%; Gibco BRL) in balanced salt solution (5 mg/ml; Sigma, St. Louis, USA) for 30 minutes at 37° C. to release the cellular fraction. Then, the collagenase was inactivated by addition of an equal volume of cell culture medium [Dulbecco's modified Eagle's medium (DMEM; Gibco BRL)] containing 10% fetal bovine serum (FBS; Gibco BRL). The cell suspension was centrifuged at 250×g for 10 minutes. Cells were resuspended in 0.16 M $NH_4Cl$ and allowed to stand for 5 minutes at room temperature (RT) for erythrocytes lysis. The mixture was centrifuged at 250×g and cells were resuspended in DMEM plus 10% FBS and 1% ampicillin/streptomycin mixture (Gibco BRL) and then they were filtered through a 40 μm mesh and were plated in tissue culture flasks at a concentration of $10\text{-}30 \times 10^3$ cells/$cm^2$.

Ex Vivo Expansion of hAD-MSCs

The previously isolated hAD-MSCs were cultured for 24 hours at 37° C. in an atmosphere of 5% $CO_2$ in air. Then, the culture flasks were washed with PBS to remove non-adhering cells and cell fragments. The cells were maintained in culture in the same medium and under the same conditions until they reached approximately 80% confluence, with replacement of the culture medium every 3 to 4 days. Cells were then passaged with trypsin-EDTA (Gibco BRL) at a dilution of 1:3 which corresponds to a cell density of approximately about $5\text{-}6 \times 10^3$ cells/$cm^2$.

1.2 Isolation and Ex Vivo Expansion of Human Bone Marrow-Derived Mesenchymal Stem Cells (hBM-MSCs)

hBM-MSCs were produced as previously described by Pittinger (Blood, 15 Feb. 2005-Volume 105, Number 4)

1.3 Immunophenotype Characterization of hAD-MSCs and hBM-MSCs

Mesenchymal stem cell populations obtained from human adipose tissue (i.e., hAD-MSCs) and from human bone marrow (hBM-MSCs) were cultured as described above. These cells showed a marked expansion after in vitro culture and exhibited a fibroblast-like morphology (FIG. 1).

In order to investigate the phenotypic characteristics of hAD-MSCs, flow cytometry studies were conducted in these cells and compared to hBM-MSCs (also analyzed by means of flow cytometry) by using the corresponding antibodies labeled with a fluorescent marker (i.e., by fluorescence immunocytometry) for the presence/absence of a series of surface markers.

Figure 2:
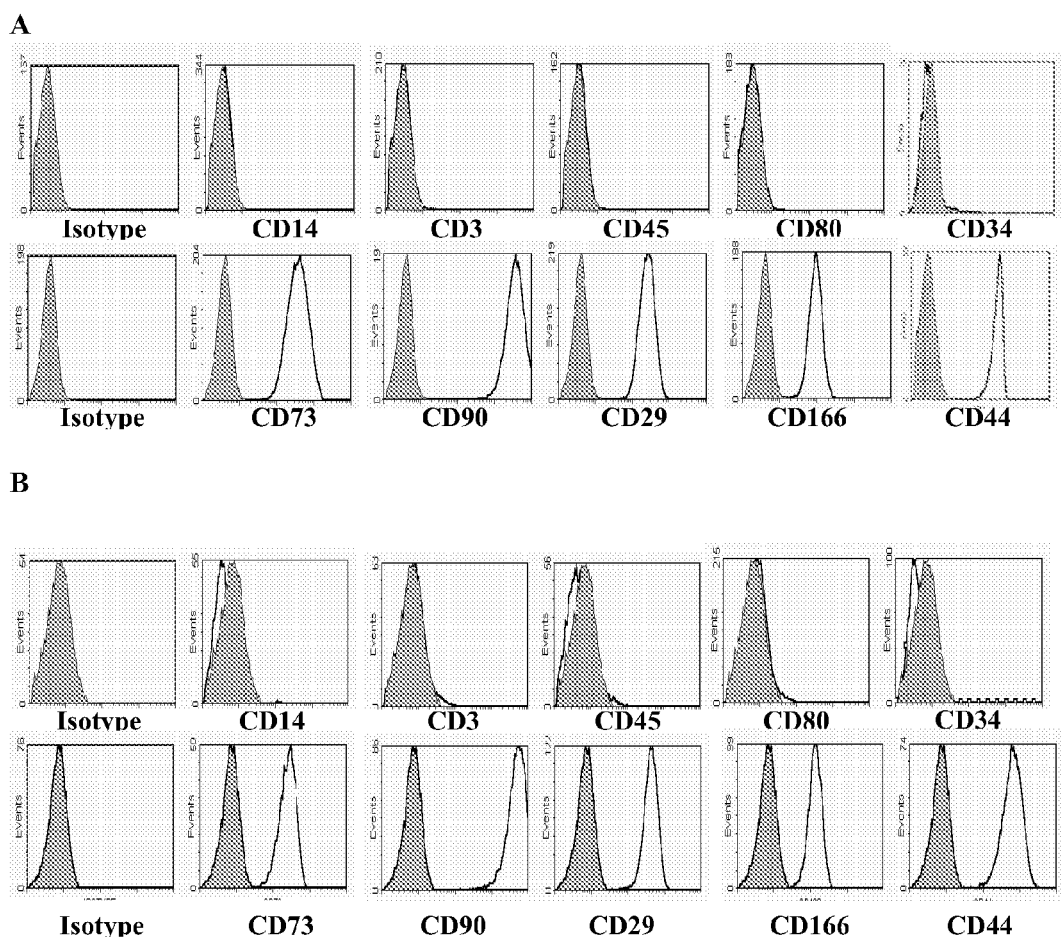
FIG. 2 shows the immunophenotype of hAD-MCs (A) and hBM-MCs (B) by FACS analysis. Cells were cultured for 5 to 7 passages, harvested and labelled with antibodies against human antigens. Shaded histograms indicate isotype-matched mouse IgG antibody control staining.

The antibodies used in the flow cytometry assay were the following:
CD3: anti-CD3, Coulter-Immunotech, USA
CD 10: anti-CD 10, Coulter-Immunotech, USA
CD11b: anti-CD11b, BD Biosciences Pharmingen, Palo Alto, Calif., USA
CD 13: anti-CD 13, Coulter-Immunotech, USA CD 14: anti-CD14, Coulter-Immunotech, USA
CD 19: anti-CD 19, Coulter-Immunotech, USA
CD29: anti-CD29, Coulter-Immunotech, USA
CD31: anti-CD31, Coulter-Immunotech, USA
CD34: anti-CD34, BD Biosciences Pharmingen, Palo Alto, Calif., USA
CD44: anti-CD44, BD Biosciences Pharmingen, Palo Alto, Calif., USA
CD45: anti-CD45, Coulter-Immunotech, USA
CD49d: anti-CD49d, Coulter-Immunotech, USA
CD49e: anti-CD49e, Coulter-Immunotech, USA
CD49f: anti-CD49f, BD Biosciences Pharmingen, Palo Alto, Calif., USA
CD54: anti-CD54, Coulter-Immunotech, USA
CD62L: anti 62L, Coulter-Immunotech, USA
CD73: anti-CD73, BD Biosciences Pharmingen, Palo Alto, Calif., USA
CD90: anti-CD90, BD Biosciences Pharmingen, Palo Alto, Calif., USA
CD95L: anti-CD95L, Caltag laboratories, Burlingame, Calif., USA
CD105: anti-CD 105, Coulter-Immunotech, USA
CD106: anti-CD 106, Coulter-Immunotech, USA
CD117: anti-CD117, Coulter-Immunotech, USA
Anti Human HLA DR: anti-Hu HLA DR, BD Biosciences Pharmingen, Palo Alto, Calif., USA
Anti Human HLA-ABC: anti-Hu HLA_ABC, BD Biosciences Pharmingen, Palo Alto, Calif., USA
CD 166: anti-CD 166, BD Biosciences Pharmingen, Palo Alto, Calif., USA
CXCR4: anti-CXCR4, BD Biosciences Pharmingen, Palo Alto, Calif., USA Representative histograms are shown in FIG. 2. Additionally, a summary of the surface markers characterizing the hAD-MSCs as compared to the hBM-MSCs are shown in Table 1. Significantly, inventors observed that under the experimental conditions of mesenchymal stem cells (MSCs) generation, both the hAD-MSCs and the hBM-MSCs were CD34 negative. They also observed that both hAD-MSCs and hBM-MSCs were also negative for CD3, CD14, CD19, CD31, CD45, CD62L, CD95L, CD117 and HLA-DR. Both types of cell preparations were always positive for CD13, CD29, CD44, CD49e, CD73, CD90, CD105, CD166 and HLA-ABC (Table 1). In the case of CD10 and CD106, Sometimes, some hBM-MSCs and hAD-MSCs (typically <20%) expressed said markers. The opposite situation was observed regarding CD49f and CD54, who were expressed in most of the hAD-MSCs, but only in a low proportion of hBM-MSCs.

TABLE I

Immunophenotype characterization of hAD-MSCs and hBM-MSCs

| Antigen | hAD-MSCs | hBM-MSCs |
|---|---|---|
| CD34 | − | − |
| CD45 | − | − |
| CD11b | − | − |
| CD14 | − | − |
| CD31 | − | − |
| CD3 | − | − |
| CD19 | − | − |
| CD117 | − | − |
| CD10 | −/+ | + |
| CD13 | + | + |
| CD44 | + | + |
| CD73 | + | + |
| CD90 | + | + |
| CD105 | + | + |
| CD106 | +/− | + |
| CD166 | + | + |
| CD29 | + | + |
| CD49d | − | − |
| CD49e | + | + |
| CD49f | + | −/+ |
| CD54 | + | −/+ |
| CD62L | − | − |
| CXCR4 | − | − |
| HLA-ABC | + | + |
| HLA-DR | − | − |
| CD95L | − | − |
| CD80 | − | − |

Example 2

Figure 3:
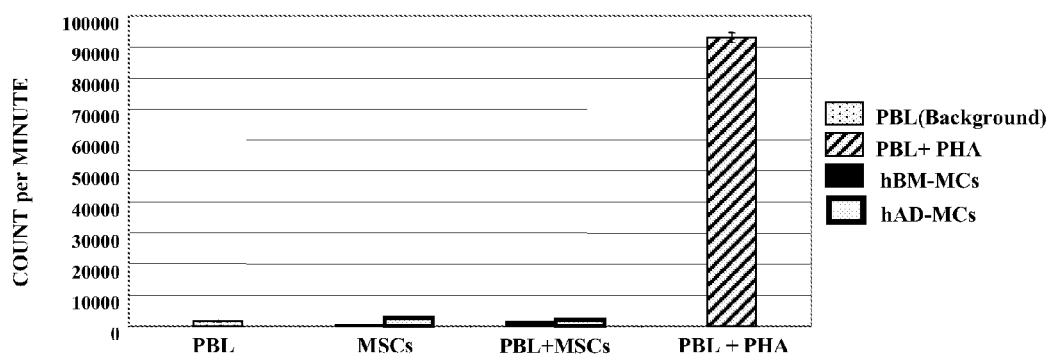
In FIG. 3 it is shown that allogeneic MSCs do not elicit a proliferative response when cultured with allogeneic peripheral blood lymphocytes (PBL). PBLs were cultured with irradiated allogeneic MSCs.

Human Adipose Tissue-Derived Mesenchymal Stem Cells (hAD-MSCs) are Non-Immunogenic In order to investigate whether or not hAD-MSCs induce a proliferative response into allogeneic lymphocytes, 10,000 peripheral blood lymphocytes (PBLs), were cultured with different numbers of hAD-MSCs (Example 1). Similar experiments were conducted with hBM-MSCs (Example 1). PBLs were obtained by Ficoll-Hypaque density gradient from heparinized peripheral blood samples of the healthy donors. $10^5$ hAD-MSCs and 105 PBLs, were cultured in complete medium at 37° C., 5% $CO_2$ for 3 days. Similarly, 105 hBM-MSCs and 105 PBLs, were cultured in complete medium at 37° C., 5% $CO_2$ for 3 days. PBLs cells were cultured in RPMI-1640 supplemented with penicillin, streptomycin, L-glutamine and 10% heat-inactivated fetal bovine serum. As a proliferation control, $1\times10^5$ PBLs in 200 µl were incubated with phytohaemagglutinin (PHA), at a final concentration of 10 µl/ml. 1 µCi of thymidine was added to each well 18 hours before harvesting the stimulated PBL, the hBM-MSCs with PBL or the hAD-MSCs with PBLs. The cells were harvested on day 3. Thymidine incorporation was measured by β-liquid scintillation counter (LKB 1205 Betaplate, Wallac). Results are expressed in counts per minute and show as mean±SD. All experiments were run in triplicate. As it is shown in FIG. 3, the presence of hAD-MSCs did not induce any proliferation of allogeneic PBLs. Similar results were obtained when hBM-MSCs were used, indicating that these two MSC types are non-immunogenic.

Example 3

Figure 4:
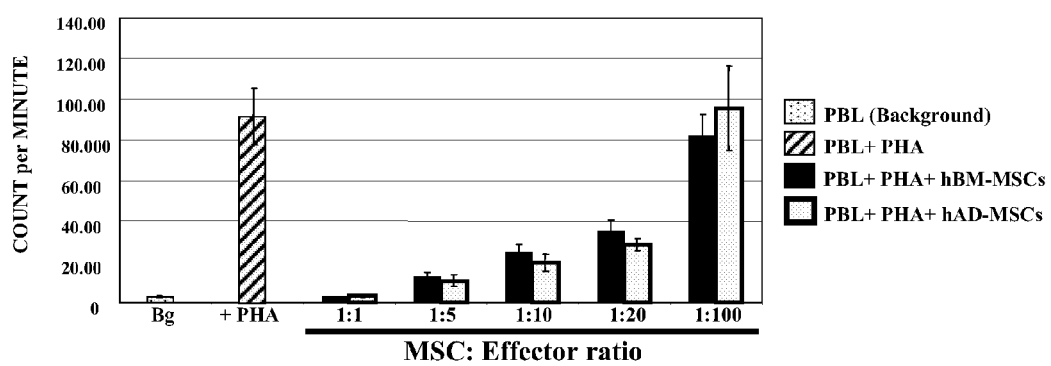
FIG. 4 represents the effects of hAD-MSCs and hBM-MSCs on lymphocyte response to mitogens. 100,000 peripheral blood lymphocytes (PBL) per well were stimulated with phytohaemagglutinin (PHA). At the beginning of the culture, hBM-MCs or hAD-MCs were added at the proportions shown in the Figure. Data are expressed as mean±SD of eight experiments, each performed in triplicate.

Human Adipose Tissue-Derived Mesenchymal Stem Cells (hAD-MSCs) Induce Immunosuppressive Effects In Vitro In a first set of experiments, the in vitro immunomodulatory effects of hAD-MSCs (Example 1) was examined by evaluating the influence of said cells to modulate the proliferative response of human PBLs (Example 2) to phytohaemagglutinin (PHA) stimulations PBLs were obtained by Ficoll-Hypaque density gradient from heparinized peripheral blood samples of the healthy donors. Separated cells were cultured in RPMI-1640 supplemented with penicillin, streptomycin, L-glutamine and 10% heat-inactivated fetal bovine serum. For mitogenic stimulation. $1\times10^5$ PBLs in 200 µl were incubated with phytohaemagglutinin (PHA), at a final concentration of 10 μl/ml. AD-MSCs were added in diminishing concentrations, at the beginning of the culture. 1 μCi of thymidine was added to each well 18 hours before harvesting. The cells were harvested on day 3. Thymidine incorporation was measured by β-liquid scintillation counter (LKB 1205 Betaplate, Wallac). Results are expressed in counts per minute and show as mean±SD. All experiments were run in triplicate. Positive controls included mitogen-stimulated PBL or MLC without MSCs. In parallel, cultures with hBM-MSCs (Example 1) were conducted as a control. Peripheral blood lymphocytes (PBLs) were obtained by Ficoll-Hypaque density gradient from heparinized peripheral blood samples of the healthy donors. Separated cells were cultured in RPMI-1640 supplemented with penicillin, streptomycin, L-glutamine and 10% heat-inactivated fetal bovine serum. For mitogenic stimulation, $1\times10^5$ PBLs in 200 μl were incubated with phytohaemagglutinin (PHA), at a final concentration of 10 μl/ml. BM-MSCs were added in diminishing concentrations, at the beginning of the culture. 1 μCi of thymidine was added to each well 18 hours before harvesting. The cells were harvested on day 3. Thymidine incorporation was measured by β-liquid scintillation counter (LKB 1205 Betaplate, Wallac). Results are expressed in counts per minute and show as mean±SD. All experiments were run in triplicate. Positive controls included mitogen-stimulated PBL or MLC without MSCs. As it is shown in FIG. 4, the proliferation of PBLs was progressively decreased as the proportion of hAD-MSCs in the culture was increased. FIG. 4 also shows that the dose-response effect mediated by hAD-MSCs was the same compared to the effect produced by hBM-MSCs. In both instances, ratios of 1 MSC:100 responder PBLs or higher had a significant non-suppressive effect on the proliferation of PBLs.

Figure 5:
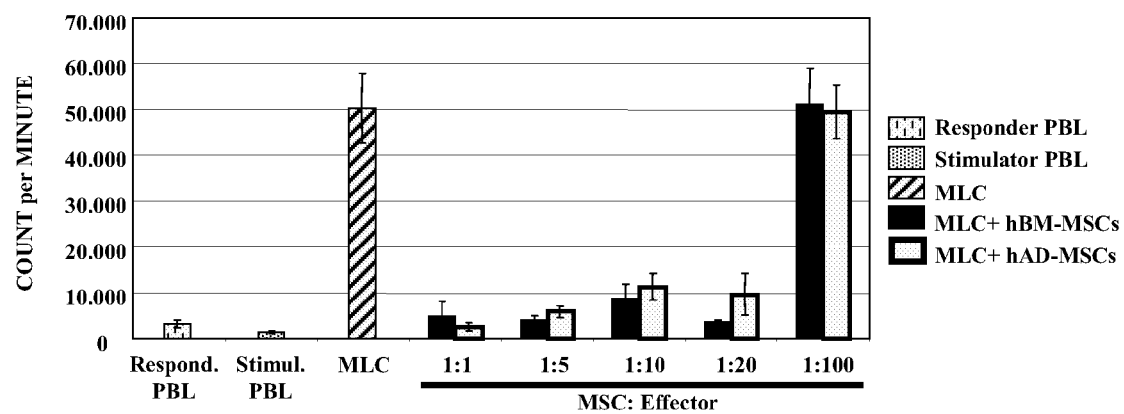
FIG. 5 shows the effect of hAD-MCs and hBM-MCs on mixed lymphocytes culture (MLC). hAD-MCs or hBM-MCs were added in diminishing concentrations to MLC (100,000 responder and stimulator PBLs, respectively). Lymphocytes proliferation was significantly suppressed when both types of MSC were added to MLC at different ratios. Mean±SD of eight experiments, each performed in triplicate.

A second set of experiments was carried out in order to investigate the modulatory effects of hAD-MSCs upon PBLs subjected to an allogeneic stimulation. Thus, irradiated PBLs (15 Gy) (effector population) were co-cultured with responder allogeneic PBLs in the presence of increasing concentrations of hAD-MSCs or hBM-MSCs. Seven days later, the proliferation activity of the responder PBLs was determined. As it was observed in PBLs subjected to PHA stimulation (FIG. 4), a dose-dependent inhibitory effect of hAD-MSCs was noticed in the responder PBLs (FIG. 5). Again, the biological activity of hAD-MSCs was similar to that found with hBM-MSCs. Both MSC types inhibited the proliferation of PBLs above 70% when ratios of at least 1:20 (MSC:responder PBLs) were used (FIG. 5).

Example 4

Figure 6:
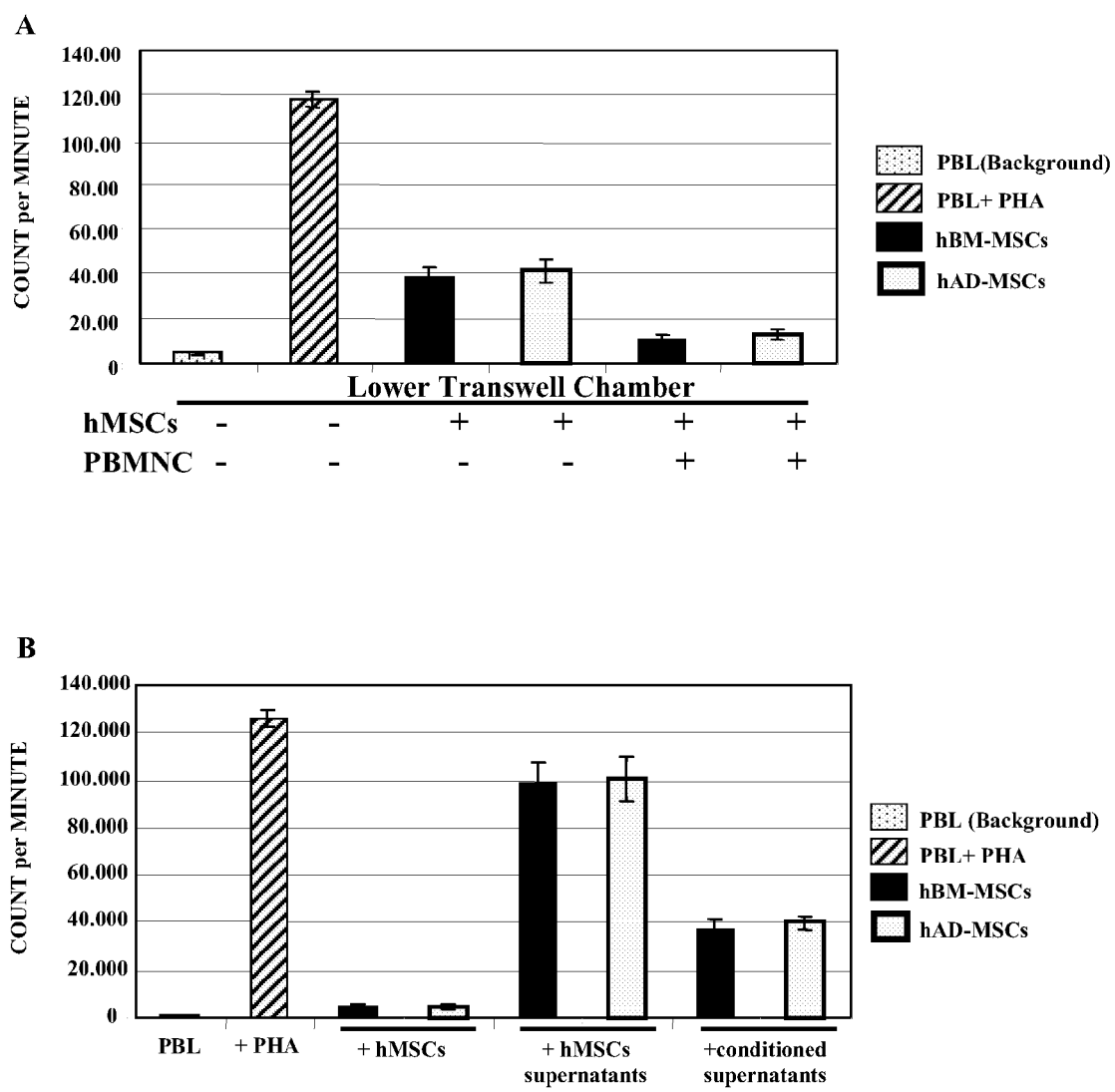
FIG. 6 illustrates that a soluble factor secreted by hAD-MCs and hBM-MCs on activation mediates the immunosuppresive effect. (A) Phytohaemagglutin (PHA)-stimulated lymphocytes were cultured in the upper chamber of a transwell. The proliferation was suppressed when hAD-MCs or hBM-MCs were cultured in lower transwell or when MCs plus PBLs were cultured in lower transwell. (B) The proliferative response was measured in the presence of hAD-MCs or hBM-MCs in direct contact with PHA-stimulated lymphocytes. The proliferation was only mildly diminished when supernatants from cultured MCs were added to the culture. However, the addition of conditioned supernatants from hMCs previously activated by a 4-day culture with allogeneic lymphocytes, showed a higher proliferation suppression, although at a lower range than the one observed in a cell-to-cell contact.

Soluble Factors from Human Adipose Tissue-Derived Mesenchymal Stem Cells (hAD-MSCs) Can Mediate the Immunosuppressive Effects that Characterize Said Cells In order to investigate whether cell-to-cell interactions between hAD-MSCs and PBLs are required for the immunosuppression mediated by these cells, transwell experiments were conducted. Briefly, PHA-stimulated PBLs were cultured in the upper chamber of a transwell, while irradiated hAD-MSCs (Example 1) remained in the lower chamber. In Transwell experiments, PHA-stimulated PBL were cultured in the upper chamber of a transwell insert, either alone or with irradiated Ad-MSCs (30 Gy) cultured in the lower chamber. MSCs were pre-plated 18 hours before addition of the stimulated PBL to produce adherent monolayers. The two types of cells were separated by a semipermeable membrane with a pore size of 0.4 μm. $^3$H-thymidine incorporation assay was performed after 3 days of culture. Thymidine incorporation was measured by β-liquid scintillation counter. In parallel, PHA-stimulated PBLs were cultured in the upper chamber of a transwell, while irradiated hBM-MSCs (Example 1) remained in the lower chamber. PHA-stimulated PBL were cultured in the upper chamber of a transwell insert, either alone or with irradiated BM-MSCs (30 Gy) cultured in the lower chamber. MSCs were pre-plated 18 hours before addition of the stimulated PBL to produce adherent monolayers. The two types of cells were separated by a semipermeable membrane with a pore size of 0.4 μm. $^3$H-thymidine incorporation assay was performed after 3 days of culture. Thymidine incorporation was measured by β-liquid scintillation counter. As it is shown in FIG. 6A, hAD-MSCs were capable of suppressing the lymphocytes proliferation in this transwell assay, demonstrating that a soluble factor is responsible for the immunosuppressive activity of hAD-MSCs. Significantly, the immunosuppressive effect of hAD-MSCs and hBM-MSCs (hAD-MSCs or hBM-MSCs) was enhanced when irradiated third-party PBLs. Peripheral blood lymphocytes (PBLs) were obtained by Ficoll-Hypaque density gradient from heparinized peripheral blood samples of the healthy donors. Separated cells were cultured in RPMI-1640 supplemented with penicillin, streptomycin, L-glutamine and 10% heat-inactivated fetal bovine serum were mixed together with said MSCs in the lower chamber of the transwells. This indicates that the physical interaction of allogeneic PBLs with the MSCs increases the suppressive activity of said cells (FIG. 6A).

In a further set of experiments the immunosuppressive effect of conditioned medium from hAD-MSCs and hBM-MSCs, after incubation either in the presence or in the absence of allogeneic lymphocytes (alloMSC-CM and MSC-CM, respectively) was investigated. To produce conditioned supernatants, $1\times10^5$ BM-MSCs or AD-MSCs were cultured in 25 cm$^2$ flask for 4 days with $5\times10^6$ allogeneic PBL. The conditioned supernatant was recovered and filtered through 0.22 μm filter. Said alloMSC-CM and MSC-CM, respectively, were added to responder PHA-stimulated lymphocytes. For mitogenic stimulation. $1\times10^5$ PBLs in 200 μl were incubated for three days with phytohaemagglutinin (PHA), at a final concentration of 10 μl/ml, and their effect on the responder population investigated as disclosed before. As it is shown in FIG. 6B, the addition of MSC-CM (either from hAD-MSCs or from hBM-MSCs) to PHA-stimulated PLBs only mediated a mild decrease in the proliferation of said cells. In contrast to this observation, a significant proliferation decrease was produced when AlloMSC-CM (either from hAD-MSCs or from hBM-MCs) was used. As it is shown in FIG. 6B, although significant, the effect was not as marked as that observed by hAD-MSCs or hBM-MSCs in direct contact with the responder PBLs. Taken together, these results confirm the similar immunosuppressive effects mediated by hAD-MSCs and hBM-MSCs. The results also show that soluble mediators are involved in this effect and indicate that the production of these factors is promoted by the interaction with allogeneic cells.

Example 5

Human Mesenchymal Stem Cells (MSCs)-Immune Interaction

Figure 7:
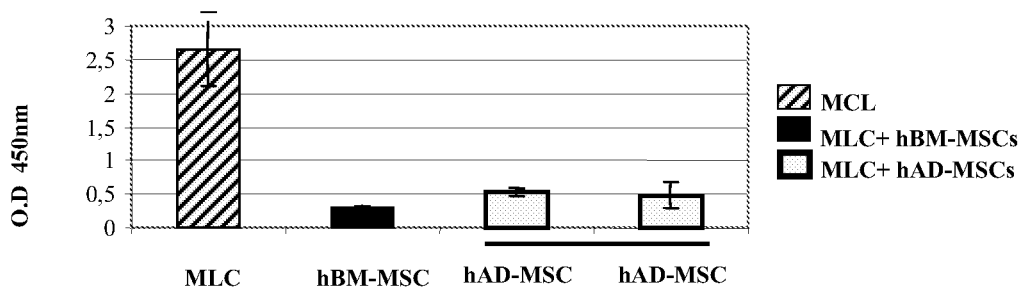
FIG. 7 shows that hMSCs decrease TNF-α and IFN-γ production on mixed lymphocytes cultures (MLC). MSCs were added in diminishing concentrations to MLC. TNF-α and IFN-γ secretion were quantified by ELISA. Fibroblasts were used as negative controls.
Figure 7:
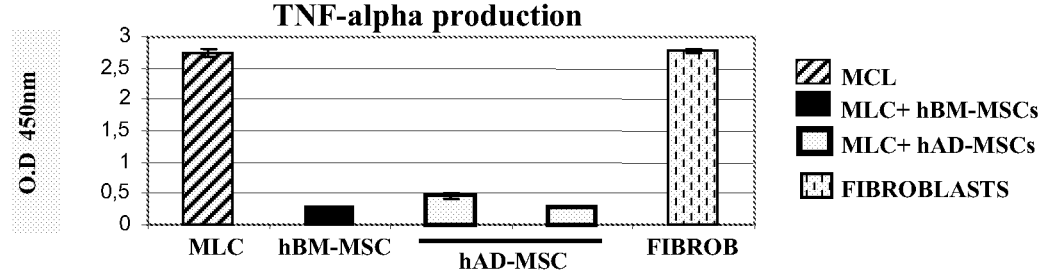

In order to understand the mechanisms of MSC-mediated immune modulation, the interactions between cultured expanded hMSC [both hAD-MSCs (Example 1) or hBM-MSCs (Example 1)] and different immune cells was examined. IFN-γ (FIG. 7A) and TNF-α (FIG. 7B) production on mixed lymphocytes culture (MLC) were quantified by ELISA technique screened by the Human INF-γ Screening Set and Human TNF-α Screening Sets (Endogen, Pierce, Rockford, Ill., USA). The measurement of TNF-α and IFN-γ production was done completely according to the protocol of the manufacturer. The secretion of both types of cytokines decreased with the addition of MSCs.

Figure 8:
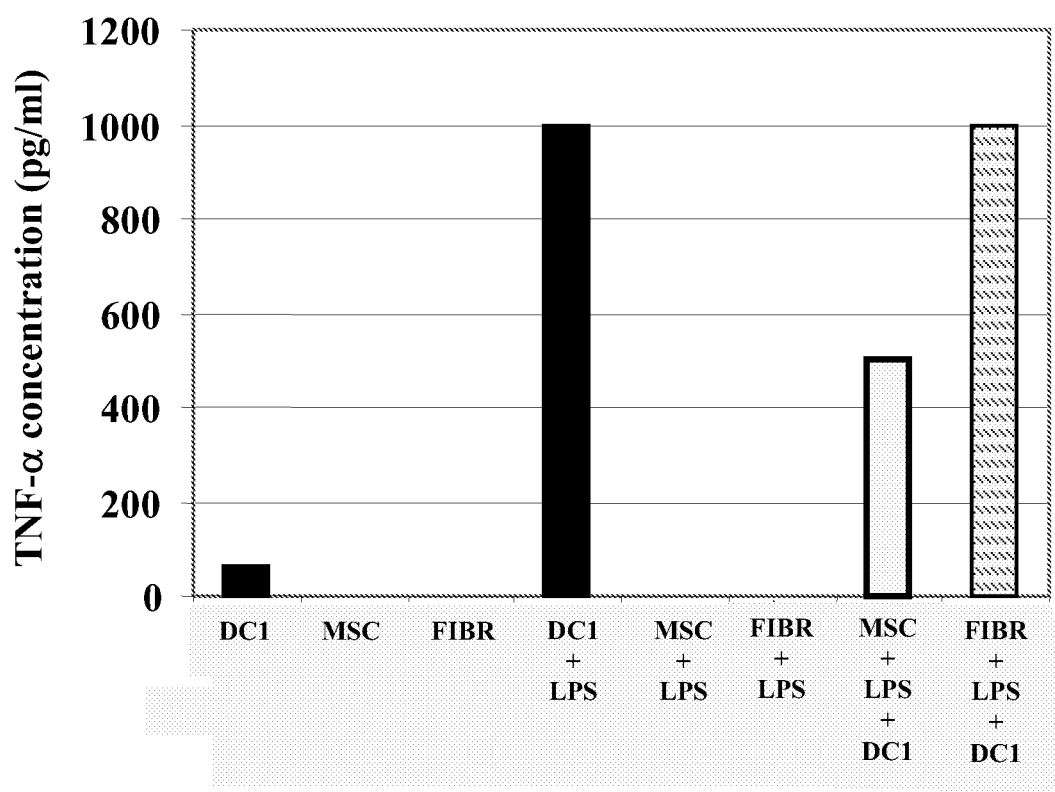
FIG. 8 shows that hMSCs reduce TNF-α secretion by dendritic cells type 1 (DC1). hMSCs were co-cultured with dendritic cells type 1 (DC1) in the presence or the absence of inflammatory stimulus (LPS). When hMSCs were present, a 50% decrease in the secretion of TNF-α by activated DC1 was detected. Fibroblasts were used as negative controls.

Dendritic cells type 1 (DC1) were obtained from monocytes as follows. Peripheral blood mononuclear cells (PBMCs) were obtained by Ficoll-Hypaque density gradient from heparinized peripheral blood samples of the healthy donors. PBMCs ($5\times10^6$ cells/ml) were added to 75 cm$^2$ flask and allowed to adhere for 2 hours. Non adherent cells were removed by gentle washing and remaining adherents cells were cultured in Roswell Park Memorial Institute (RPMI)-1640 medium (Gibco, N.Y., USA) supplemented with L-glutamine, penicillin, streptomycin (Gibco), as well as GM-CSF (100 ng/ml) and IL-4 (100 ng/ml). On day 3, 50% of medium was replaced by fresh medium containing twofold higher concentration of the cytokines. The cells were cultured during 7 days. After 7 days of induction with Granulocyte Macrophage-Colony Stimulating Factor (GM-CSF) (Chemicon International, Temecula, Calif., USA) plus interleukin 4 (IL-4) (Chemicon International, Temecula, Calif., USA), these dendritic cells (DC1) were stimulated by lipopolysaccharide (LPS) (Sigma-Aldrich fine Chemicals, St. Louis, Mo., USA) for additional 48 hours, co-cultured with or without MSCs. Culture cell-free supernatants were collected and quantified by ELISA for TNF-α production (Endogen, Pierce, Rockford, Ill., USA). FIG. 8 shows the percentage of decrease in TNF-α levels when hMSCs (both hAD-MSCs or hBM-MSCs) were co-cultured with the activated DC1. The inhibition of TNF-α secretion by DC1 impedes their maturation, migration to lymph nodes and ability to stimulate allo-T.

Example 6

Immunophenotype Characterization of Mouse Adipose Tissue-Derived Mesenchymal Stem Cells (mAD-MSCs)

As conducted with hAD-MSCs, the phenotype of mouse adipose tissue-derived mesenchymal stem cells (mAD-MSCs) incubated under conditions described above was investigated by flow cytometry. The method for the generation of the murine adipose derived mesenchymal stem cells mAD-MSCS is similar to the one used for the generation of the human MSCs. Murine mesenchymal stem cells were obtained from C57 BL-Balb-c (Jackson laboratories, USA), but can be obtained from the fat of any mouse normal strain. The antibodies used in the flow cytometry assay were the following:

CD11b: anti-CD11b clone M1/70, BD Biosciences Pharmingen, Palo Alto, Calif., USA.

CD29: anti-CD29 clone Ha2/5, BD Biosciences Pharmingen, Palo Alto, Calif., USA.

CD31: anti-CD31 clone MEC13.3, BD Biosciences Pharmingen, Palo Alto, Calif., USA.

CD34: anti-CD34, BD Biosciences Pharmingen, Palo Alto, Calif., USA.

CD44: anti-CD44 clone IM7, BD Biosciences Pharmingen, Palo Alto, Calif., USA.

CD45.1: anti-CD45.1 clone A20, BD Biosciences Pharmingen, Palo Alto, Calif., USA.

CD45.2: anti-CD45.2 clone 104, BD Biosciences Pharmingen, Palo Alto, Calif., USA.

CD49e: anti-CD49e clone 5H10-27, BD Biosciences Pharmingen, Palo Alto, Calif., USA.

CD80: anti-CD80 clone 16-10A1, BD Biosciences Pharmingen, Palo Alto, Calif., USA.

CD90: anti-CD90 CLONE 53-2.1, BD Biosciences Pharmingen, Palo Alto, Calif., USA

CD117: anti-CD117 clone 2B8, BD Biosciences Pharmingen, Palo Alto, Calif., USA.

GR.1: anti-GR-1 clone RB6-8C5, BD Biosciences Pharmingen, Palo Alto, Calif., USA.

Sca-1: anti-Sca1 clone E13-161.7, BD Biosciences Pharmingen, Palo Alto, Calif., USA.

Figure 9:
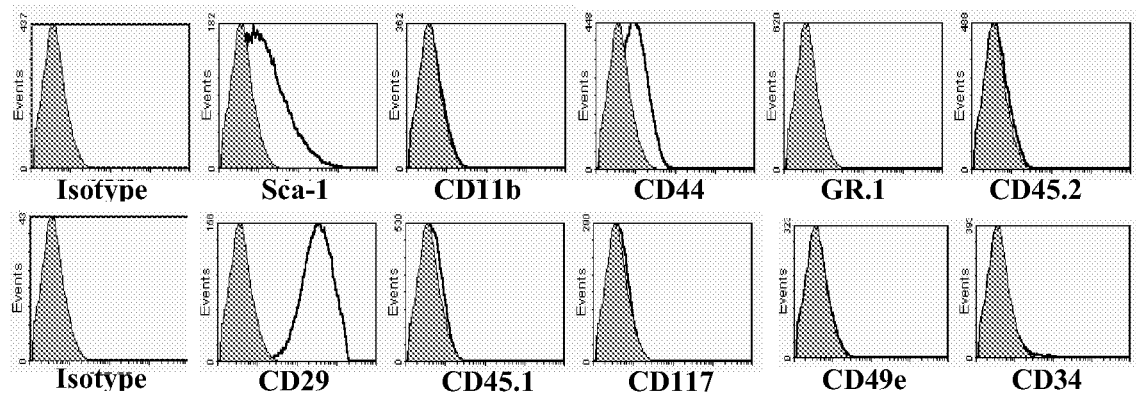
FIG. 9 shows the immunophenotype of mAD-MCs. Cells were stained with antibodies against murine antigens. Shaded histograms indicate isotypes-matched mouse IgG antibody control staining.

Representative histograms are shown in FIG. 9. Additionally, a summary of the surface markers is presented in Table 11. As it is shown in FIG. 9, mAD-MSCs were negative for the endothelial markers (CD31 and CD117), as well as for the hematopoietic markers (CD34, CD45, CD11b and GR.1). These cells, however, expressed moderate levels of Sca-1 and CD44, and were positive for the expression of CD29 and CD90.

TABLE II

Immunophenotype characterization of mAD-MSCs

| Antigen | mAD-MSCs |
| --- | --- |
| CD34 | − |
| CD11b | − |
| CD45.1 | − |
| CD45.2 | − |
| GR.1 | − |
| CD31 | − |
| Sca-1 | −/+ |
| CD90 | + |
| CD117 | − |
| CD44 | −/+ |
| CD29 | + |
| CD49e | − |
| CD80 | − |

Example 7

Figure 10:
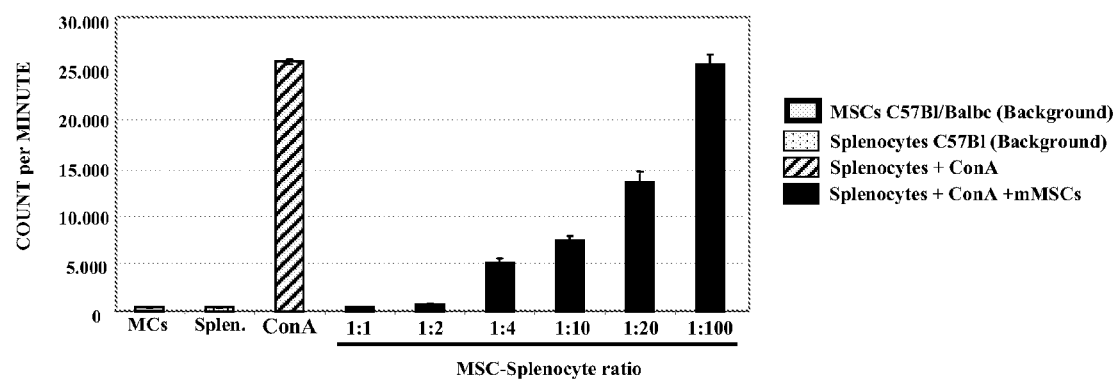
FIG. 10 shows that murine adipose-derived MSCs (mAD-MCs) inhibit a proliferative response in allogeneic (A) or autologous (B) splenocytes in a dose-dependent manner. C57Bl (A) or C57Bl/Balbc (B) splenocytes were incubated for 4 days with concavaline A (ConA). At the beginning of the culture, mAD-MCS were added in diminishing concentrations. Mean±SD of two experiments, each performed in triplicate.
Figure 10:
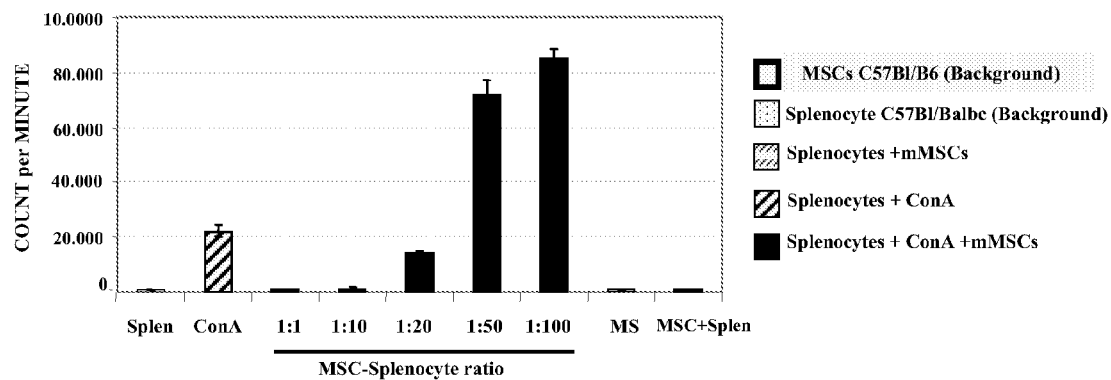

Mouse Adipose Tissue-Derived Mesenchymal Stem Cells (mAD-MSCs) Induce Immunosuppressive Effects In Vitro The immunologic properties of mAD-MSCs from F1 (C57Bl/Balbc) mice (Jackson Laboratories, USA) were investigated in a proliferative assay using Concavaline-A (Con-A)-stimulated splenocytes from C57Bl or C57Bl/Balbc mice (Jackson Laboratories, USA). Splenocytes were obtained by disgregating the spleens, washing of the cells, lysis of the remaining red blood cells, washing of the pure splenocytes and counting of the viable cells by trypan blue. Responding 105 splenocytes were incubated for 4 days with Concavaline A (ConA), with or without mAD-MSCs, in diminishing concentrations. As it is shown in FIG. 10, the addition of mAD-MSCs inhibited the ConA-induced proliferative response of the responder splenocytes. As observed with hAD-MSCs, the suppression of the proliferative response occurred in a dose-dependent manner in both autologous and allogeneic cells.

Example 8

Figure 11:
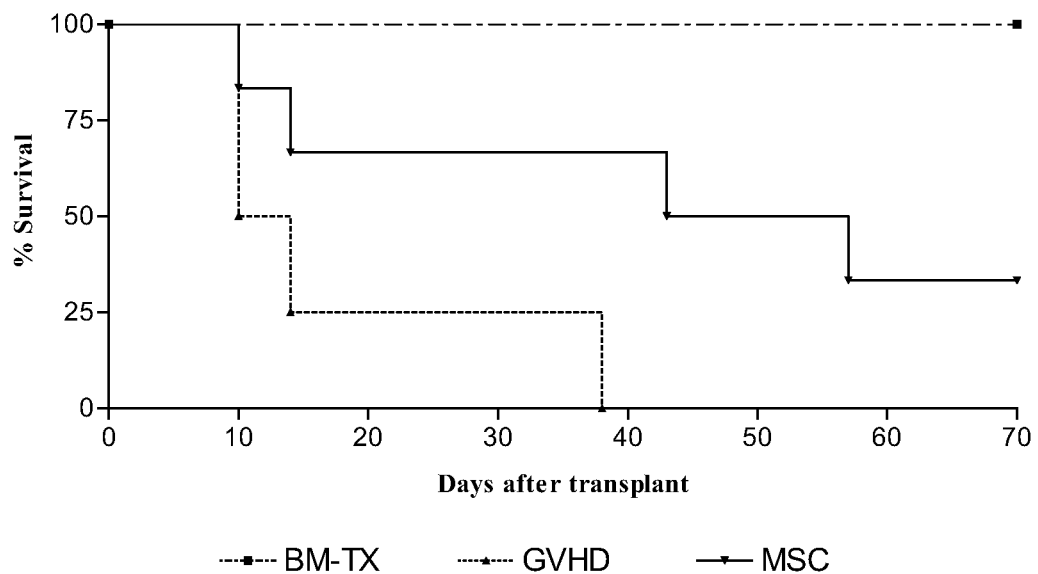
In FIG. 11 a survival curve is represented. Irradiated F1(C57Bl/Balbc) recipient mice received $1 \times 10^7$ bone marrow cells from C57Bl mice, with or without $2 \times 10^7$ splenocytes from the donor, to induce GVHD. One group of recipient mice received additional intravenous (i.v.) infusions of $5 \times 10^5$ mouse AD-MCs. Compared to the control group, the severity of the GVHD was significantly reduced in mice receiving mAD-MCs

Mouse Adipose Tissue-Derived Mesenchymal Stem Cells (mAD-MSCs) Induce Immunosuppressive Effects In Vivo Next, it was studied whether the in vitro findings were of significance in an in vivo mouse model of haploidentical transplantation. In these experiments irradiated F1 (C57Bl/Balbc) were divided in three groups. Group 1 was infused with $1 \times 10^7$ bone marrow cells (BM) from C57Bl mice. Bone marrow cells were obtained from the flushing out of the tibias and femurs of C57Bl mice, washed and diluted in a saline solution. Group 2 received $1 \times 10^7$ bone marrow plus $2 \times 10^7$ splenocytes from the same donor, in order to induce graft versus host disease (GVHD). Group 3 mice were transplanted with $1 \times 10^7$ bone marrow plus $2 \times 10^7$ splenocytes, and received additional intravenous (i.v.) infusions of $5 \times 10^5$ mAD-MSCs (Example 6), administered at periodic 7 days intervals administered for up to 28 days post-transplant. While none of the animals from Group 1 died after transplantation, all animals from Group 2 died from GVHD before 40 days post-transplantation (FIG. 11). Remarkably, a significant improvement in mice survival was produced as a consequence of the infusion of mAD-MSCs. These results are consistent with all the in vitro data shown above, and indicate that mAD-MSCs constitute an immunosupresive reagent capable of modulating strong immunoresponses not only mediated by a polyclonal stimulation, but also but other stimulations, such as allogeneic stimulation. This indicates that AD-MSCs (at least, the hAD-MSCs or mAD-MSCs with the phenotype described herein) constitute a new immunomodulatory reagent for the prophylaxis and treatment of GVHD in patients transplanted with allogeneic grafts. Additional applications of said AD-MSCs derived from the immunosuppressive effects herein described are obvious for the skilled person in the art.

The invention claimed is:

1. A method of reducing severity or treating graft-versus-host disease (GVHD) in a mammal given a bone marrow transplant (BMT), the method comprising administering a pharmaceutical composition to the mammal given the BMT, wherein the pharmaceutical composition comprises:
   i) a therapeutically or prophylactically effective amount of an adipose derived mesenchymal stem cell (AD-MSC) population that is:
      (a) negative for CD3, CD11 b, CD14, CD19, CD31, CD34, CD45, CD62L, CD95L, CD117, and HLA-DR cell surface markers, and
      (b) positive for CD13, CD29, CD44, CD49e, CD73, CD90, CD105, CD166, and HLA-ABC cell surface markers, and
   ii) a pharmaceutically acceptable vehicle.

2. The method of claim 1, wherein said pharmaceutical composition is administered in combination with an additional pharmaceutical composition for the treatment of graft-versus-host disease.

3. The method of claim 2, wherein said additional pharmaceutical composition is administrated simultaneously or sequentially to the pharmaceutical composition comprising an adipose tissue derived cell population.

4. The method according to claim 1, wherein said graft-versus-host disease is selected from the group consisting of chronic graft-versus-host disease and acute graft-versus-host disease.

5. The method according to claim 1, wherein said pharmaceutical composition is a pharmaceutical composition for parenteral administration.

6. The method according to claim 1, wherein said cell population is from human origin.

7. The method according to claim 1, wherein the mammal is human.

* * * * *

UNITED STATES PATENT AND TRADEMARK OFFICE
CERTIFICATE OF CORRECTION

PATENT NO. : 8,440,177 B2
APPLICATION NO. : 12/096456
DATED : May 14, 2013
INVENTOR(S) : Manuel Angel González De La Peña et al.

It is certified that error appears in the above-identified patent and that said Letters Patent is hereby corrected as shown below:

In the Claims

Column 22, Line 32: change "6. The method according to claim 1, wherein said cell" to --6. The method according to claim 1, wherein said AD-MSC--

Signed and Sealed this
Ninth Day of July, 2013

Teresa Stanek Rea
*Acting Director of the United States Patent and Trademark Office*